United States Patent
Teller et al.

[11] 3,944,580
[45] Mar. 16, 1976

[54] 7-[2-(DITHIOCARBOXYLAMINO)ALKANAMIDO]-CEPHALOSPORANIC ACID DERIVATIVES

[75] Inventors: Daniel M. Teller, Devon; John H. Sellstedt, Pottstown; Charles J. Guinosso, King of Prussia, all of Pa.

[73] Assignee: American Home Products Corporation, New York, N.Y.

[22] Filed: Oct. 17, 1974

[21] Appl. No.: 515,751

[52] U.S. Cl. .......... 260/243 C; 260/302 S; 424/246
[51] Int. Cl.² ............... C07D 501/28; C07D 501/34
[58] Field of Search .................................. 260/243 C

[56] References Cited
UNITED STATES PATENTS
3,855,211  12/1974  Breuer et al. ................... 260/243 C OTHER PUBLICATIONS
Lewis et al., Antimicrobial Agents & Chemeotherapy–1968, pp. 109–114 (1969).
Sassiver et al., Antimicrobial Agents & Chemeotherapy, 1968, pp. 101–108 (1969).

*Primary Examiner*—Richard J. Gallagher
*Assistant Examiner*—Diana G. Rivers
*Attorney, Agent, or Firm*—Richard K. Jackson

[57] ABSTRACT

Compounds of the formula:

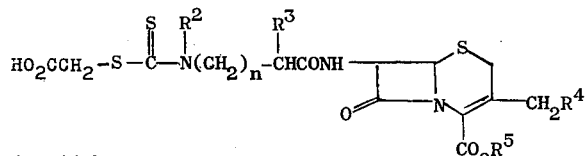

in which
$R^2$ is —H or alkyl of 1 to 6 carbon atoms;
$R^3$ is —H, alkyl of 1 to 6 carbon atoms or phenyl;
$R^4$ is —H, alkanoyloxy of 2 to 6 carbon atoms, or

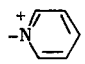

when $R^5$ is —H;
$R^5$ is —H or an alkali metal;
$n$ is one of the integers 0 and 1;
or an alkali metal salt thereof,
are gram positive and gram negative antibacterial agents.

4 Claims, No Drawings

7-[2-(DITHIOCARBOXYLAMINO)ALKANAMIDO]-CEPHALOSPORANIC ACID DERIVATIVES

DESCRIPTION OF THE INVENTION

In accordance with this invention there is provided a group of antibacterial agents of the formula

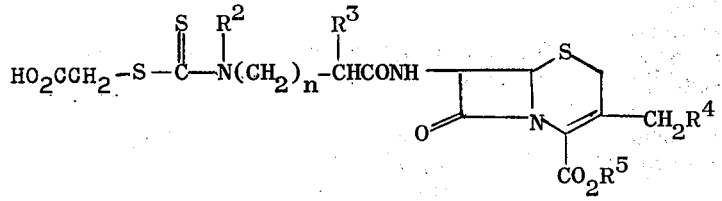

derivative with an appropriately substituted precursor acid derivative of the formula:

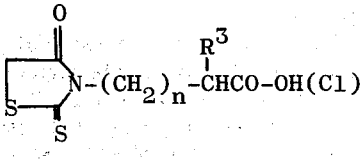

in which
R[2] is —H or alkyl of 1 to 6 carbon atoms;
R[3] is —H, alkyl of 1 to 6 carbon atoms or phenyl;
R[4] is —H, alkanoyloxy of 2 to 6 carbon atoms, or

when R[5] is —H;
R[5] is —H or an alkali metal;
n is one of the integers 0 and 1; or an alkali metal salt thereof.

The alkali metal intended to be embraced by the preceding description of the compounds of this invention is either sodium or potassium. The alkyl groups contain from 1 to 6 carbon atoms and include such radicals as methyl, ethyl, n-propyl, i-propyl, n-butyl, t-butyl, n-pentyl, n-hexyl and the like. The expression lower alkanoyloxy embraces the lower fatty acyloxy moieties such as acetoxy, propanoyloxy, butanoyloxy, amyloxy, hexanoyloxy, and the like.

The N-carboxymethyl esters of this invention are prepared by a base induced ring opening of a 7-[(4-oxo-2-thioxo-3-thiazolindinyl) acetamido]cephalosporanic acid derivative of Formula I The latter reaction procedes smoothly in an inert organic solvent at a temperature of from about −40° to about +25°C. When the free carboxylic acid is employed, the reaction is performed in the presence of a condensing agent such as carbonyl diimidazole; dicyclohexylcarbodiimide; dicyclohexylcarbodiimide in the presence of N-hydroxysuccinimide or 1-hydroxybenzotriazole; isobutylchloroformate; and the like. These and similar condensing agents which are operable in the preparation of the antibacterial agents of this invention are presented in Spencer et al., J. Med. Chem. 9, pp. 746–750 (1966); Micetich et al., J. Med. Chem. 15, pp. 333–335 (1972); Klausner et al., Synthesis, pp. 453–463 (1972) and U.S. Pat. No. 3,338,896.

Alternatively, the precursor carboxylic acid derivative may be converted by known means to an acid halide which is then used in aqueous medium to acylate the free amino group of either a tertiary amine salt or an alkali metal salt of the 7-amino-cephalosporanic acid. In addition, the carboxylic acid halide precursor may be used to react in organic solution with either a tertiary amine salt or a silylated, phosphorylated or saccharinated derivative of the 7-amino-cephalosporanic acid derivative.

The precursor carboxylic acid derivatives are prepared by the method of Zuber et al., Helv. Chim. Acta., 35, 1744 (1952); Minka, Farmat sevt. Zh. (Kiev) 18(5), 32–5 (1963); C.A. 60, 5476a; or Brown, Chem. Rev., 61, 463 (1961). The generally preferred scheme is:

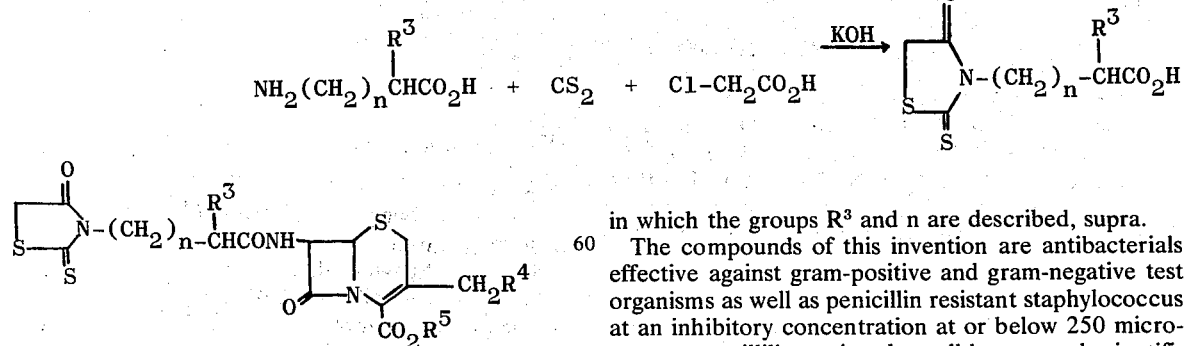

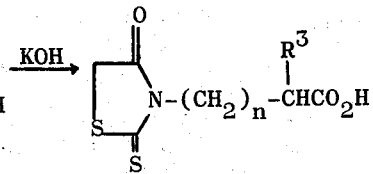

in which R[3], R[4], R[5] and n are defined above. Compounds of Formula I are prepared by coupling the appropriately substituted 7-amino-cephalosporanic acid in which the groups R[3] and n are described, supra.

The compounds of this invention are antibacterials effective against gram-positive and gram-negative test organisms as well as penicillin resistant staphylococcus at an inhibitory concentration at or below 250 micrograms per milliliter using the well-known and scientifically accepted agar serial dilution technique. The compounds have also been shown to be active in vivo. Thus, the compounds of this invention are useful in the fields of comparative pharmacology and microbiology and may be used in the treatment of bovine mastitis, as growth promotors in animals and for the treatment of infections amenable to treatment with penicillins and cephalosporins.

The in vivo activity of the antibacterial agents of this invention was established by subcutaneously administering a dose of the compound being tested at zero time and 6 hours after infection to a randomized group of mice which had been infected with a specific infective agent, such as *Escherichia coli*, etc., via intraperitoneal injection of 0.5 milliliters of the infective agent in 5 per cent gastric mucin. The mice were then observed for 14 days and any deaths were recorded daily. The curative dose ($CD_{50}$) was then reported in terms of the milligrams per mouse needed for complete control of the infective agent.

The following examples are presented for purposes of illustration and should not be construed as limitations upon the true scope of this invention. The biological activity data presented after each example illustrates the compounds activity against specific bacteria of the designated strain in terms of the minimum inhibitory concentration of the compound in micrograms per milliliter to completely inhibit the test organism.

The abbreviations for the bacteria employed in the testing are as follows:

ST AU — *Staphylococcus aureus*
BA SU — *Bacillus subtilis*
NE CA — *Neisseria catarrhalis*
SA PA — *Salmonella paratyphi*
KL PN — *Klebsiella pneumoniae*
ES CO — *Escherichia coli*
BO BR — *Bordetella brochiseptica*
ES IN — *Escherichia intermedia*
PR VU — *Proteus vulgaris*
PR MI — *Proteus mirabilis*
SA TY — *Salmonella typhosa*
SH SO — *Shigella sonnei*

EXAMPLE 1

7-[2-(Dithiocarboxyamino)acetamido]cephalosporanic acid N-carboxymethyl ester

To a slurry of 7-[(4-oxo-2-thioxo-3-thiazolidinyl)-acetamido]cephalosporanic acid (12.0 g, 0.027 moles) in water (170 ml) is added dropwise at 5°C. sodium hydroxide (54.0 ml of 1.00 M solution, 0.054 moles) over 30 minutes. During the addition the pH rises from 2.5 initially to 8.2 and dissolution takes place. The solution is filtered and freeze-dried to give the title compound as the disodium salt, 13.50 g. orange solid; mp. 130°–280°C. (d);

$\lambda_{max}^{KBr}$ 5.62, 6.18 $\mu$; $\lambda_{max}^{EtOH}$ 260 m$\mu$ ($\epsilon$9,600), 294 m$\mu$ ($\epsilon$ 4,860);

NMR has 2.12, 3.93 and 4.49 ppm singlets.

Elemental Analysis for $C_{15}H_{15}N_3O_8S_3Na_2.2H_2O$: Calc'd: C, 33.15; H, 3.52; N, 7.73; S, 17.71; $H_2O$, 6.63. Found: C, 33.93; H, 3.40; N, 7.74; S, 15.19; $H_2O$, 5.40.

Acidification of the disodium salt affords the title compound.

| Bacterium | Strain | MIC ($\mu$g/ml) |
|---|---|---|
| BA SU | 663 | .244 |
| ST AU | 6538P | .976 |
| ST AU | Smith | .976 |
| ST AU | CHP | 3.90 |
| ST AU | 53-180 | 3.90 |
| NE CA | 8193 | 250 |

-continued

| Bacterium | Strain | MIC ($\mu$g/ml) |
|---|---|---|
| ES CO | 9637 | 62.5 |
| ES IN | 65-1 | 250 |
| SA PA | 11737 | 7.81 |
| KL PN | 10031 | 31.3 |
| BO BR | 4617 | 15.6 |
| PR VU | 6896 | 15.6 |

The in vivo curative dose ($CD_{50}$) from several tests averaged for:

| Bacterium | Strain | $CD_{50}$(mg) |
|---|---|---|
| ES CO | 920 | 4.48 |
| PR MI | PR-3 | 1.96 |
| SA TY | SAD-12 | 1.41 |
| ST AU | Smith | 4.37 |
| SH SO | SH-1 | 2.66 |

EXAMPLE 2

7-[3-(Dithiocarboxyamino)propionamido]cephalosporanic acid N-carboxymethyl ester Using the method described in Example 1 but substituting 7-[3-(4-oxo-2-thioxo-3-thiazolidinyl)propionamido]cephalosporanic acid (4.59 g, 0.01 moles) for 7-[(4-oxo-2-thioxo-3-thiazolidinyl)acetamido]-cephalosporanic acid and 20.0 ml of 1.00 M sodium hydroxide solution after freeze-drying gives the title compound, as the disodium salt 5.32 g. orange solid; mp 140°–145°C. (d);

$\lambda_{max}^{KBr}$ 5.65, 5.80 (shoulder), 6.23 $\mu$; $\lambda_{max}^{EtOH}$ 260 m$\mu$ ($\epsilon$10,800);

NMR has 2.12 and 3.85 ppm singlets.

Elemental Analysis for $C_{16}H_{17}N_3O_8S_2Na_2.2H_2O$: Calc'd: C, 34.47; H, 3.80; N, 7.53; S, 17.25; $H_2O$, 6.47. Found: C, 34.89; H, 3.70; N, 7.56; S, 17.68; $H_2O$, 5.02.

| Bacterium | Strain | MIC ($\mu$g/ml) |
|---|---|---|
| BA SU | 663 | .488 |
| ST AU | 6538P | .976 |
| ST AU | Smith | .976 |
| ST AU | CHP | 3.90 |
| ST AU | 53-180 | 3.90 |
| NE CA | 8193 | 125 |
| ES CO | 9637 | 15.6 |
| SA PA | 11737 | .976 |
| KL PN | 10031 | 31.3 |
| BO BR | 4617 | 7.81 |
| PR VU | 6896 | 1.95 |

EXAMPLE 3

7-[2-(Dithiocarboxyamino)phenylacetamido]cephalosporanic acid N-carboxymethyl ester Using the method described in Example 1 but substituting 7-[(4-oxo-2-thioxo-3-thiazolidinyl)-phenylacetamido]cephalosporanic acid (1.0 g, 0.00192 moles) for 7-[(4-oxo-2-thioxo-3-thiazolidinyl)acetamido]cephalosporanic acid and 3.80 ml of 1.00 M sodium hydroxide solution after freeze-drying gives the title compound, 0.95 g brown solid; mp. 140°–148°C. (d);

$\lambda_{max}^{KBr}$ 5.65, 6.20 $\mu$; NMR has 2.12 and 3.88 ppm singlets.

Elemental Analysis for $C_{21}H_{19}N_3O_aS_3Na_2 \cdot 1\frac{1}{2}H_2O$: Calc'd: C, 41.31; H, 3.63; N, 6.88; S, 15.75. Found: C, 41.04; H, 3.73; N, 6.69; S, 13.64.

The title compound exhibited in vivo activity at a $CD_{50}$ of 6.0 milligrams/mouse against ES CO-920.

| Bacterium | Strain | MIC ($\mu$g/ml) |
|---|---|---|
| BA SU | 663 | 3.90 |
| ST AU | 6538P | 7.81 |
| ST AU | Smith | 7.81 |
| ST AU | CHP | 31.3 |
| ST AU | 53-180 | 15.6 |
| NE CA | 8193 | 250 |
| ES CO | 9637 | 31.3 |
| ES IN | 65-1 | 250 |
| SA PA | 11737 | 15.6 |
| EN AE | 13048 | 250 |
| KL PN | 10031 | 31.3 |
| BO BR | 4617 | 125 |
| PR VU | 6896 | 7.81 |

What is claimed is:

1. A compound of the formula:

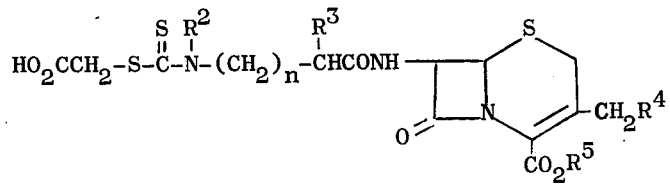

in which $R^2$ is —H or alkyl of 1 to 6 carbon atoms;
$R^3$ is —H, alkyl of 1 to 6 carbon atoms or phenyl;
$R^4$ is —H, alkanoyloxy of 2 to 6 carbon atoms, or

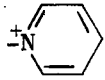

when $R^5$ is —H;
$R^5$ is —H or an alkali metal;
$n$ is one of the integers 0 and 1;
or an alkali metal salt thereof.

2. The compound of claim 1, which is 7-[2-(dithiocarboxyamino)acetamido]cephalosporanic acid N-carboxymethyl ester or an alkali metal salt thereof.

3. The compound of claim 1, which is 7-[3-(dithiocarboxyamino)propionamido]cephalosporanic acid N-carboxymethyl ester or an alkali metal salt thereof.

4. The compound of claim 1 which is 7-[2-(dithiocarboxyamino-2-phenyl)acetamido]cephalosporanic acid N-carboxymethyl ester or an alkali metal salt thereof.

* * * * *